United States Patent [19]

Fishman

[11] Patent Number: 5,588,441

[45] Date of Patent: Dec. 31, 1996

[54] ALLERGY TESTING APPARATUS WITH VARIABLY SPACED TEST USING SITES

[76] Inventor: Henry Fishman, 5173 Linnean Ter. NW., Washington, D.C. 20008

[21] Appl. No.: 479,791

[22] Filed: Jun. 7, 1995

Related U.S. Application Data

[63] Continuation of Ser. No. 13,679, Feb. 3, 1993, abandoned, which is a continuation-in-part of Ser. No. 931,202, Aug. 17, 1992, Pat. No. 5,335,670, which is a continuation of Ser. No. 685,626, Apr. 15, 1991, Pat. No. 5,154,181, which is a continuation of Ser. No. 501,376, Mar. 29, 1990, Pat. No. 5,027,826, which is a continuation of Ser. No. 339,863, Apr. 14, 1989, abandoned, which is a continuation of Ser. No. 204,967, May 31, 1988, abandoned, which is a continuation of Ser. No. 88,139, Aug. 21, 1987, abandoned, which is a continuation of Ser. No. 853,710, Apr. 18, 1986, Pat. No. 4,711,247.

[51] Int. Cl.$^6$ ........................................ A61B 5/00
[52] U.S. Cl. ........................................ 128/743
[58] Field of Search ........................ 128/743; 604/46, 604/47, 191; 606/181–183, 185, 186

[56] References Cited

U.S. PATENT DOCUMENTS

| | | | |
|---|---|---|---|
| 2,522,309 | 9/1950 | Simon | 128/743 |
| 3,289,670 | 12/1966 | Krug et al. | 128/743 |
| 3,556,080 | 1/1971 | Hein | 128/743 |
| 3,741,197 | 6/1973 | Sanz et al. | 606/182 |
| 4,237,906 | 12/1980 | Havstad et al. | 128/743 |
| 4,711,247 | 12/1987 | Fishman | 128/743 |
| 5,027,826 | 7/1991 | Fishman | 128/743 |
| 5,076,282 | 12/1991 | Fishman et al. | 128/743 |
| 5,097,810 | 3/1992 | Fishman et al. | 128/743 |
| 5,139,029 | 8/1992 | Fishman et al. | 128/743 |
| 5,154,181 | 10/1992 | Fishman | 128/743 |
| 5,179,959 | 1/1993 | Fishman et al. | 128/743 |
| 5,335,670 | 8/1994 | Fishman | 128/743 |

*Primary Examiner*—Max Hindenburg
*Attorney, Agent, or Firm*—Frishauf, Holtz, Goodman, Langer & Chick

[57] ABSTRACT

An allergy testing technique for testing a patient for a plurality of substances includes a first member having a plurality of pik engaging portions arranged for selectively engaging respective piks for pricking or piercing the skin of a patient in use. A resilient compressible member is coupled to the first member for controlling a downward movement distance of the first member and for consequently controlling a downward movement distance of the piks. A well tray has a plurality of receptacles for receiving substances for which a patient is to be tested. The first member with the piks engaged thereon, is engageable with the well tray for causing the piks to contact substances in respective associated receptacles, the first member being thereafter removed from the well tray. The first member is then placed against the skin of a patient and is pressed downwardly (either straight down or with a rocking motion) against the skin of the patient to compress the compressible member and to cause the piks to contact the skin of the patient and to apply the substances at respective spaced apart positions on the skin of the patient. The first member preferably has a plurality of openings therein for selectively receiving elongated pik members in the openings. The first member also has indicia thereon for uniquely identifying the openings, and the well tray receptacles are similarly uniquely identified with indicia.

39 Claims, 9 Drawing Sheets

ALLERGY TESTING APPARATUS WITH VARIABLY SPACED TEST USING SITES

This application is a Continuaton of application Ser. No. 08/013,679 filed Feb. 3, 1993, which is a Continuation-In-Part of application Ser. No. 07/931,202 filed Aug. 17, 1992, now U.S. Pat. No. 5,335,670, which is a Continuation of Ser. No. 07/685,626 filed Apr. 15, 1991 (now U.S. Pat. No. 5,154,181) which is a Continuation of Ser. No. 07/501,376 filed Mar. 29, 1990 (now U.S. Pat. No. 5,027,826), which is a Continuation of Ser. No. 07/339,863 filed Apr. 14, 1989 (abandoned), which is a Continuation of Ser. No. 07/204,967 filed May 31, 1988 (abandoned), which is a Continuation of Ser. No. 07/088,139 filed Aug. 21, 1987 (abandoned), which is a Continuation of Ser. No. 06/853,710 filed Apr. 18, 1986 (now U.S. Pat. No. 4,711,247). The entire contents of application Ser. No. 07/931,202 are incorporated herein by reference.

BACKGROUND OF THE INVENTION

This invention relates to allergy testing apparatus and methods, and more specifically to improved apparatus and methods for testing a patient for a plurality of allergies at substantially the same time, and which enables a practitioner to variably space the testing sites on the skin of a patient with great convenience.

Various allergy testing devices for simultaneously testing a patient for a number of substances substantially at the same time are known, from, for example, prior U.S. Pat. Nos. 4,711,247; 5,027,826; 5,154,181; 5,076,282; 5,097,010; and 5,139,029. An object of the present invention is to provide a further improved apparatus and method for testing patients for allergic reactions to a plurality of substances, all at substantially the same time, and which allows varying the spacing between testing sites on the skin of a patient in a simple and convenient manner, while also using a simplified structural arrangement for the testing device. The invention reduces the time required for testing, enables the practitioner to have complete freedom of choice of substances used in the tests and spacing between the testing substances, and minimizes patient discomfort, expense and inconvenience, thereby improving efficiency and improving the overall testing procedure.

Yet another object of the invention, is to provide a system having disposable needles or "piks" which are low in cost and which are easily used, and wherein the system eliminates the risk of cross-contamination and spread of infectious diseases.

A further object of the invention is to provide a system having controlled penetration of the piks or pricking devices relative to the skin of the patient being tested.

Still another object of the invention is to provide an allergy testing system wherein a well tray can be loaded in the practitioner's office or pre-loaded with antigens and sealed, for easy shipping of the well tray without danger of leakage, and without danger of contamination of the antigens contained therein.

SUMMARY OF THE INVENTION

According to the present invention an allergy testing apparatus for testing a patient for a plurality of substances comprises a first member having a plurality of engaging means arranged at respective positions on the first member for selectively engaging a respective pricking or piercing means; a plurality of pricking or piercing means which are selectively engaged with selected engaging means of the first member, at selected positions on the first member, for pricking or piercing the skin of a patient in use; and resilient compressible means coupled to the first member for controlling a downward movement distance of the first member and for consequently controlling a downward movement distance of the pricking or piercing means. A well tray means has a plurality of receptacles for receiving substances for which a patient is to be tested, the selected receptacles corresponding in position to the pricking or piercing means which are engaged with the selected engaging means at selected positions of the first member. The first member with the pricking or piercing means engaged thereon, is engageable with the well tray means for causing the pricking means mounted to the first member to contact the substances in respective associated receptacles, the first member being thereafter removable from the well tray means for application of the substances to a patient. The removed first member is then placed against the skin of a patient and is pressed downwardly against the skin of the patient to compress the compressible means and to cause the pricking or piercing means to contact the skin of the patient and to apply the substances at respective spaced apart positions on the skin of the patient, the respective spaced apart positions on the skin of the patient being spaced apart a distance corresponding to the positions at which the pricking or piercing means are engaged with the first member.

A method of testing a patient for a plurality of allergies at substantially the same time, comprises providing a first member having a plurality of engaging means arranged at respective positions on the first member; providing a plurality of pricking or piercing means which are selectively engageable with the selected engaging means of the first member, at selected positions on the first member, for pricking or piercing the skin of a patient in use; and providing a well tray means having a plurality of receptacles for respectively receiving substances for which a patient is to be tested. Respective receptacles of the well tray means are loaded with substances for which a patient is to be tested. A plurality of pricking or piercing means are engaged in engaging means of the first member which are in registration with the receptacles of the well tray means in which substances have been loaded and the first member is engaged with the well tray means to cause the plurality of pricking or piercing means to contact the substances in the loaded receptacles of the well tray means. The first member is then removed from engagement with the well tray means; and the first member, after removal from the well tray means, is placed against the skin of a patient for applying substances which have contacted the pricking or piercing means to the skin of the patient by pressing down or rocking the first member against the skin of the patient.

DETAILED DESCRIPTION

Figure 1:
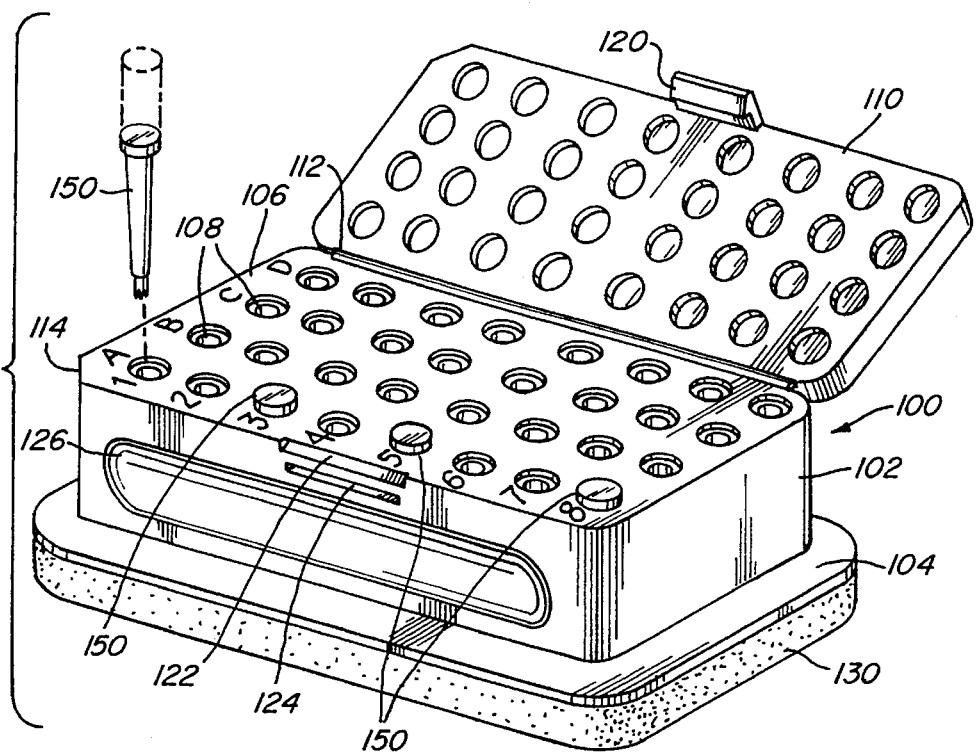
FIG. 1 is a perspective view of a holder according to the present invention in which several "piks" or pricking devices are shown loaded therein, and wherein one pik or pricking device is shown just prior to loading therein.
Figure 7:
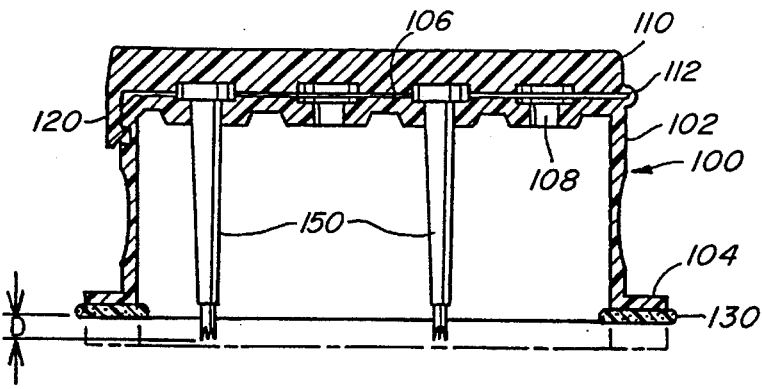
FIG. 7 is a cross-sectional view showing the holder applied to a skin surface with the resilient portion thereof compressed, showing how the depth of penetration is controlled during use.
Figures 8, 9A, 9B:
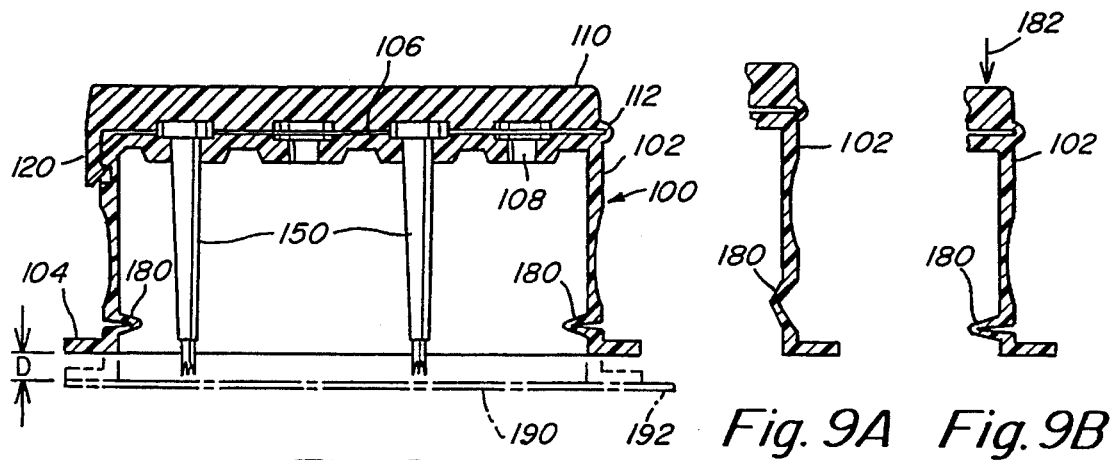
FIG. 8 is a cross-sectional view, similar to FIG. 7, showing a bellows-type resilient portion for controlling application and depth of penetration.
FIGS. 9A and 9B show the resilient bellows-type portion of FIG. 8 in the uncompressed and compressed states, respectively.

Referring to the drawings, FIG. 1 shows an allergy testing apparatus according to the present invention which comprises a holder 100 having a base portion 102 with a flange 104 extending around the base portion. The base portion 102 has an upper surface 106 having a large number of openings or holes 108 therein for receiving elongated "piks" or pricking members 150, which will be described in detail hereinbelow. See FIGS. 7 and 8 for illustrations of typical piks or pricking member 150 for use in the present invention. Throughout the following description, the pricking members or devices 150 are referred to simply as "piks" for ease of description. The piks 150 are inserted, from the top of holder 100, by a practitioner into selected openings 108, as desired, in order to vary the spacing between adjacent piks and thereby vary the spacing between testing sites on the skin of a patient. FIGS. 7 and 8 show sectional views of the apparatus showing piks 150 mounted in the holder 100. A snap-fit arrangement could also be provided to retain the piks 150 in the holes 108 of the base portion 102.

The holder 100 further comprises a cover member 110 which is hingedly connected to the base portion 102, for example by means of an integrally molded "living hinge" member 112. After a predetermined number of piks 150 are inserted into selected holes 108, the cover 110 is pivotally closed over the upper surface 106 of the lower portion 102 of the holder 100 to fix the piks in place and to stabilize the piks 150 to prevent tipping or other movement of the piks relative to the holder 100 during use. After closing of the cover 110, downward pressure is applied by the user so that the snap closure member 120 slides over the inclined guide surface 122 on the holder 100 and snappingly engages in the depression 124 in a side surface of the lower portion 102 of the holder 100. This snapping engagement, which is due to the slight resiliency of closure member 120 (made of molded plastic), insures positive closure of the cover 110 and positive retention and stabilization of the piks 150 in the desired positions. Obviously, other snap-type closure designs could be used to retain cover 110 in its closed position.

Thumb and finger grips 126 which may comprise depressed portions, are provided on opposite sides of the side walls of the base portion 102 of the holder 100, as shown in FIG. 1. Protruding or other type grip members could be provided, as desired.

Figure 2:
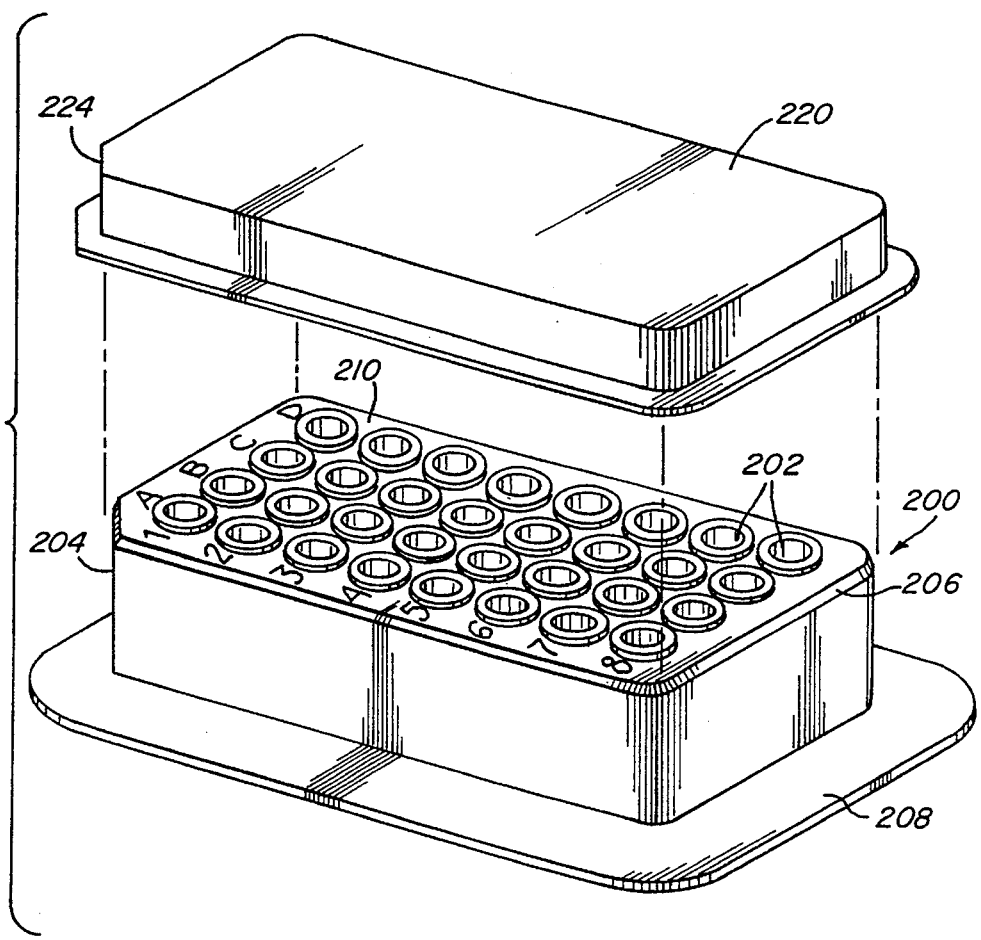
FIG. 2 shows a well tray for use in the present invention, over which the holder of FIG. 1 is mountable.
Figure 3:
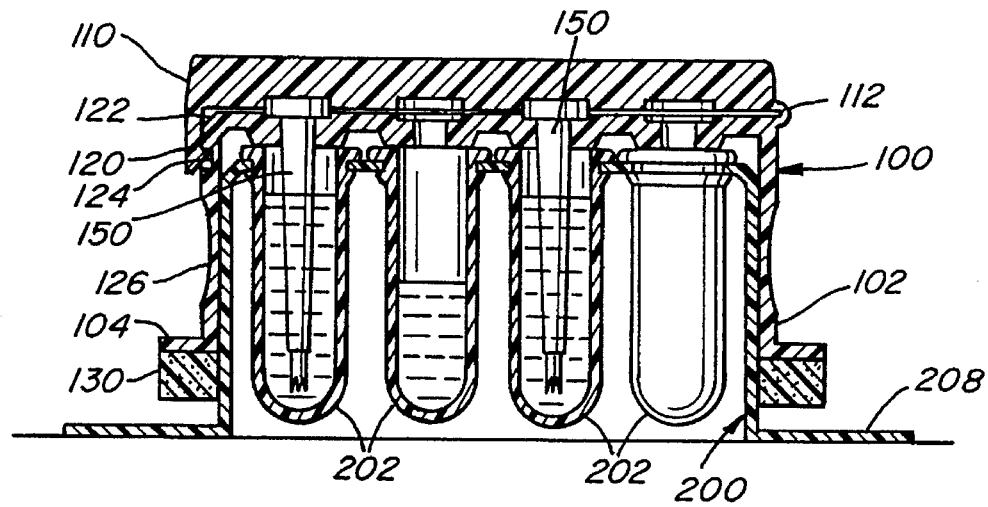
FIG. 3 is a cross-sectional view showing the well tray of FIG. 2 with a holder of FIG. 1 mounted thereover, illustrating how the piks or pricking devices are inserted into an allergen.

After the piks 150 are loaded into the holder 100, as shown by way of example in FIG. 1, the holder 100 is placed over a well tray 200, for example shown in FIG. 2. FIG. 3 shows the holder 100 placed over the well tray 200. The well tray of FIGS. 2 and 3 comprises a large number of antigen containers 202 either previously mounted therein or manually mounted into selective openings of the well tray by a practitioner. The antigen containers 202 are mounted in positions corresponding to the locations of the loaded piks 150 of the holder 100.

Figure 6:
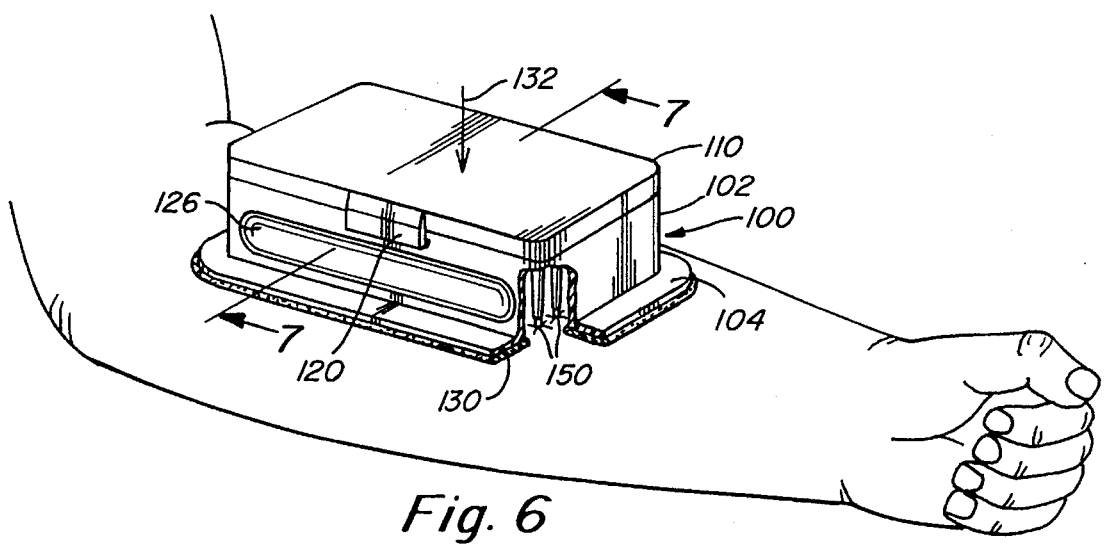
FIG. 6 shows a holder, already loaded with piks and antigens, placed against the skin of a patient for applying allergens to the skin of a patient.

A foam member (strip) 130 (i.e. foam rubber or foamed plastic) is provided on the underside of lower flange 104. The foam strip 130 may be attached to flange 104 by an adhesive. The foam strip 130 is resilient and serves as a foam spring and also serves as a positive locating device when placing the apparatus on the skin of a patient. When the apparatus is placed on the skin of a patient, for example as shown in FIG. 6, the foam strip 130 prevents slippage along the skin of the patient, while permitting relocation of the device on the skin without pricking the skin. After the device is located in the desired position, the device is pressed down in the direction of the arrow 132 in FIG. 6 to compress the foam strip 130. In addition to pressing down, or as an alternative, the device could be rocked side-to-side and/or front-to-back. Both processes, pushing down and/or rocking, will lower the pricking end portions of the piks 150 to prick the skin of a patient and to thereby apply the antigens, for example as shown in FIG. 6 and as also illustrated in FIGS. 7 and 8. The pricking may be the conventional pricking or may be intradermal. If intradermal pricking is desired, piks 150 with longer and wider teeth are used.

Referring again to FIG. 2, the well tray 200 has a flattened corner surface 204 which is designed to engage a flattened corner surface 114 of the holder 100. This insures that the holder 100 is always placed in the proper orientation over the well tray 200 in order to apply antigens to the piks 150. As readily seen from FIGS. 1 and 2, the holder 100 can be mounted over the well tray 200 in only a single orientation, defined by the location of the flat surfaces 204, 114. The upper surface of the holder 200 has a bevelled or chamfered corner 206 for easy alignment and insertion of the holder thereover. A large flange 208 is provided at the lower portion of the well tray 200 to stabilize same during use, to prevent tipping, etc. Rubber cushions (not shown) or other gripping devices can be applied to the under-surface of the flange 208 to prevent slippage or inadvertent movement on a surface.

The upper surface 106 of holder 100, and the upper surface 210 of well tray 200 have markings thereon to positively identify each particular opening thereof. See, for example, FIGS. 1 and 2, wherein the columns of openings are designated by the letters A, B, C and D, and wherein the rows of openings are designated by numerals 1–8, respectively. This matrix-type labeling arrangement enables easy and positive determination of the location of the piks in the holder 100, and the location of the corresponding wells of antigens in the well tray 200. For example, FIG. 1 shows piks loaded in positions A3, A5 and A8, and another pik about to be loaded into position A1. Therefore, in use, corresponding antigens would be located in the wells A1, A3, A5 and A8 of the well tray by the practitioner.

FIG. 2 also shows a cover 220 for the well tray 200 which should be used when the well tray is not in use. The cover 220 may be air tight to provide an airtight seal over the well tray to protect any antigens therein or to keep the interior of the well tray clean. The cover has a flat corner surface 224 which engages with the flat corner surface 204 of the well tray thereby providing registration and positive orientation of the cover 220 over the well tray 200. The positive orientation of the cover is desired in order to prevent mixing of antigen sources or cross-contamination, if the cover is used one time in a first orientation and another time in a second orientation. According to the present invention, it is possible to apply the cover with only a single orientation relative to the well tray 200.

FIG. 3 shows in greater detail the well tray 200 and holder 100 with the holder 100 mounted on the well tray to apply antigens to the piks 150 mounted therein. As shown in FIG. 3, the well tray has openings in the upper surface thereof, into which are inserted antigen containers which are generally in the shape of small test tubes, the antigen containers having a groove at the upper portion thereof so that they snap into the openings in the upper surface of the well tray, as shown in FIG. 3. Also as shown in FIG. 3, the antigen can be loaded only to a certain level in the antigen containers 202 since the antigen level rises when the piks 150 are inserted therein, also as shown in FIG. 3. After the antigens are applied to the piks, as shown in FIG. 3, the holder 100 is lifted upwardly by the practitioner, and is then ready to be applied to the skin of a patient, as shown, for example in FIG. 6.

Figure 4:
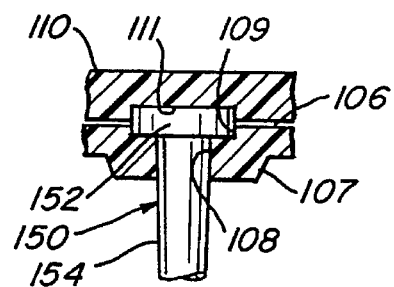
FIG. 4 shows details of a stabilizing means for stabilizing the piks held in the holder.

As mentioned above, it is necessary to stabilize the positions of the piks 150 relative to the holder 100. The stabilizing technique of FIG. 1 is shown in greater detail in FIG. 4 which shows a cross-sectional view of the stabilizing portion for a single pik 150. As shown in FIG. 4, each of the openings 108 of the upper surface 106 has a widened portion 109 into which a widened upper portion 152 of the pik 150 is received. Also, the lower portion of the opening 108 is slightly tapered to match the taper of the body portion 154 of the pik 150, thereby further providing surface-to-surface contact over the thickened shoulder portion 107 of the upper surface 106. As seen in FIG. 4, a further portion of the upper widened area 152 of the pik projects above the upper surface 106. This further portion is received in a blind depression 111 in the upper cover 110. By this technique, when the cover 110 is closed over the upper surface 106 of the holder, the pik 150 is positively stabilized in the wider openings 109 and 111, and in the tapered opening portion 108, thereby preventing tipping or other movement of the piks 150 relative to the holder during use.

Figure 5:
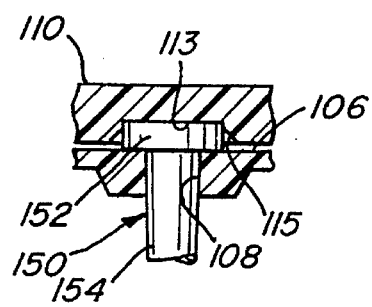
FIG. 5 is another detail showing a modified stabilizing means.

FIG. 5 shows a modified embodiment wherein the upper surface 106 of the holder has no openings 109 therein, but is merely a flat upper surface with a single opening 108 which is tapered to match the taper of the elongated body portion 154 of the pik 150. The cover 110 has a deeper depression 113 therein into which the upper widened portion 152 of the pik is received when the cover 110 is closed over the upper surface 106 of the holder. As seen in FIG. 5, the opening 113 has a chamfered edge surface 115 which facilitates closing of the cover 110 over the piks 150, thereby rendering the device easier to use. In this manner, when the cover 110 is closed over the upper surface 106 of the holder, the piks 150 are positively stabilized relative to the holder.

As seen from FIGS. 4 and 5, when the cover 110 is opened after the device has been used, and it is desired to dispose of the piks 150, the piks 150 can be gripped by the portions of the widened area 152 thereof which project above the upper surface 106 of the holder. In the embodiment of FIG. 5, removal is easier since a larger portion of the widened area 152 of the piks is exposed, and is easier to grip for removal. Removal may be by either gripping the upper portions 152 of the piks by hand, by using tweezers, or by using a specially made tool (i.e., to be inserted into the upper hollow or opening portion of the piks, or to grip the outside of the upper portions 152 of the piks 150) for removal and disposal of the piks.

FIG. 7 shows an enlarged cross-section of the device along the line 7—A in FIG. 6, showing the foam strip 130 in its compressed and uncompressed state, thereby clearly showing the depth of penetration D of the pointed ends of the piks 150 during use. FIG. 7 also clearly shows the arrangement wherein piks 150 are inserted selectively in some openings of the matrix, and also showing empty holes wherein no piks are inserted.

FIGS. 8, 9A and 9B shown a modified arrangement of the invention wherein the side walls 102 of the holder 100 have bellows-type spring members which serve as springs and which also control the depth of penetration of the piks 150 during use. FIG. 8 shows the bellow members 180 in their compressed state in solid lines and in their uncompressed state in chain lines. FIGS. 9A shows the bellows 180 in the uncompressed state, and FIG. 9B shows the bellows 180 in its compressed state when a force is applied along the direction of the arrow 182 to apply the antigens to the skin of a patient. The bellows 180 is fabricated integrally with the side wall 102 of the holder 100, for example during molding of the plastic holder. During molding, reduced thickness portions are provided so that the members 180 can serve as spring members using the resilient memory effect of the plastic material from which the holder 100 is molded. After the downward force is released, the bellows have sufficient springiness to lift the upper surface of the holder in the upward direction, away from the skin of the patient, thereby providing a clearance between the tip ends of the piks 150 and the skin of the patient, thereby enabling easy and safe removal of the device from the skin of the patient. A similar release effect takes place when using the foam strip 130, as shown in FIG. 7.

Figure 10:
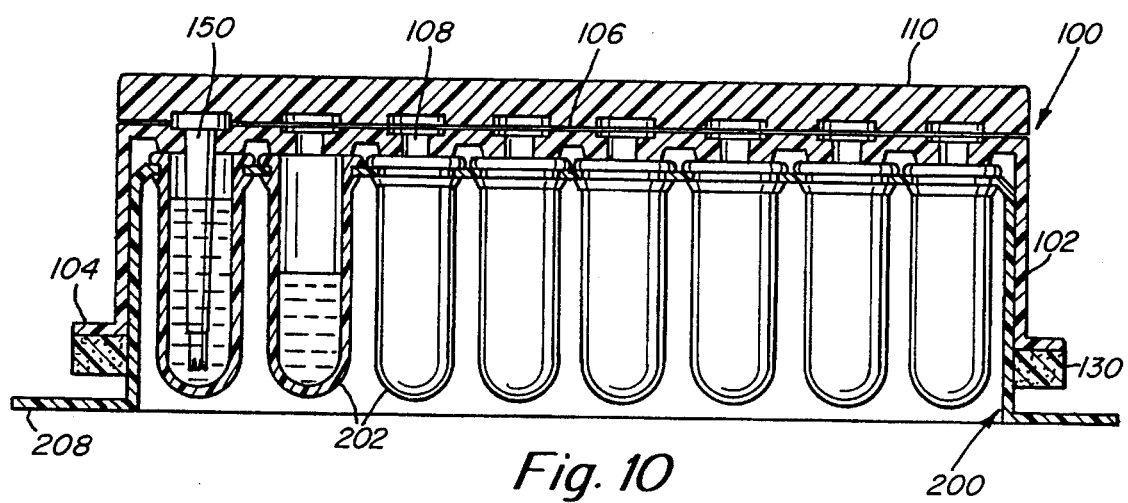
FIG. 10 is a cross-sectional view, similar to FIG. 3, but taken longitudinally of the well tray for containing antigens.
Figure 11:
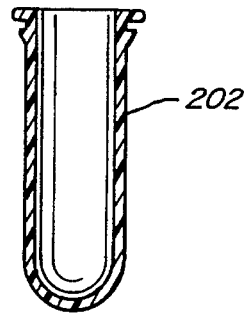
FIG. 11 shows an antigen container for use in the well tray of FIG. 10.

FIGS. 10 and 11 show a cross-sectional view of the apparatus of the present invention, with the holder mounted over a well tray, the cross-sectional view being taken in the longitudinal direction of the device. FIG. 11 shows a sectional view of the antigen container in greater detail, showing how it may be inserted into openings of the well tray in close proximity to each other in order to achieve a high density of antigens and a corresponding high density of needles, as desired, thereby providing a greater degree of variation for the practitioner concerning the location of the test sites on the skin of a patient.

Figure 12:
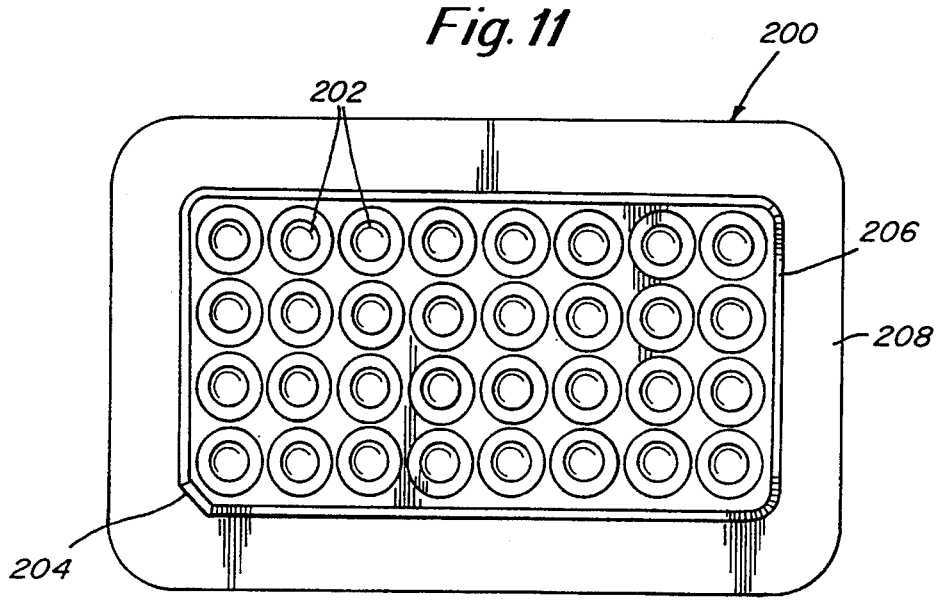
FIG. 12 is a top view of the well tray of FIG. 10 showing 32 wells and a stabilizing flange for preventing tipping of the well tray in use.

FIG. 12 is a top view of the apparatus of FIG. 10 showing the well tray with the holder removed therefrom.

Figure 13:
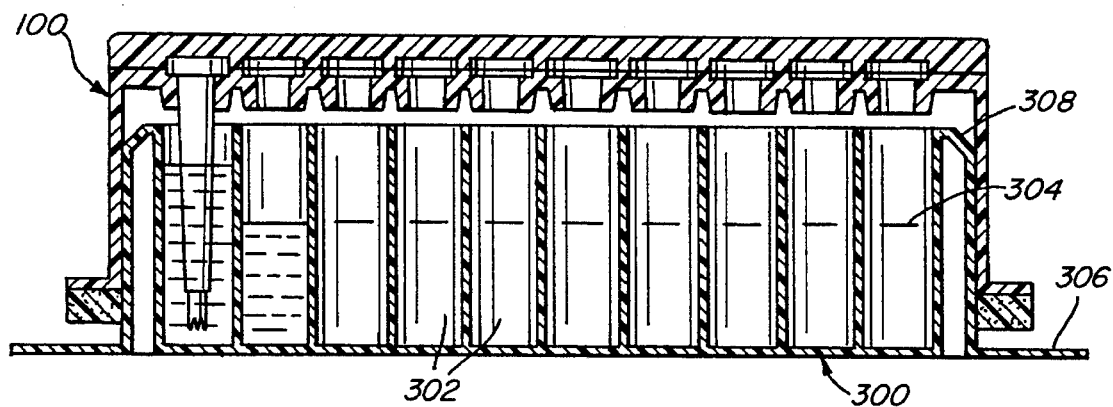
FIG. 13 shows a modified well tray with a holder placed thereover, in cross-section, and which has integrally formed antigen receiving wells formed therein, which enables a higher density of wells for a given size well tray.
Figure 14:
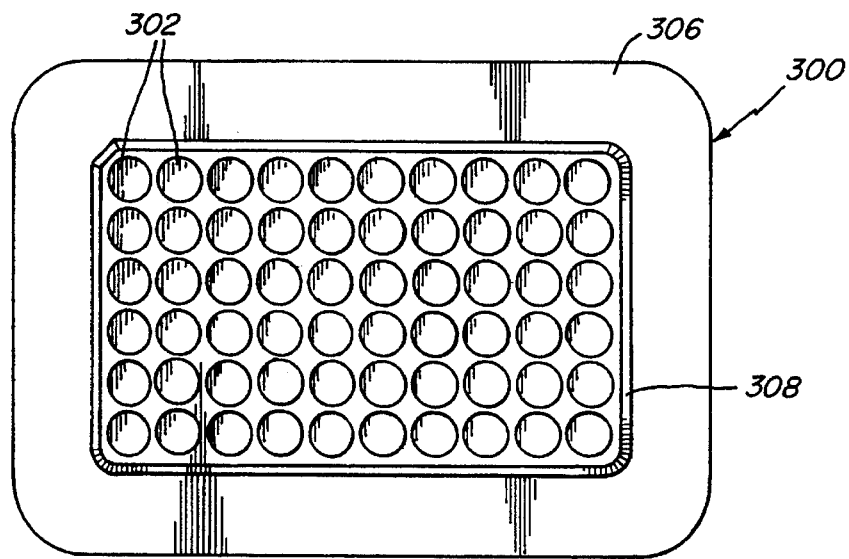
FIG. 14 is a top view of the well tray of FIG. 13.

FIG. 13 shows another embodiment of the well tray which is integrally formed with antigen container portions. The embodiment of FIG. 13 utilizes the same holder 100 as shown in FIG. 1, but may be scaled down in size since the wells in FIG. 13 may be arranged closer together (with a higher density) than in the well tray of FIGS. 2 and 10. As shown in FIG. 13, the integrated well tray 300 is a single integral molded member having a large plurality of circular (or rectangular, if desired) receptacles 302 therein (see the top view of FIG. 14). Antigens are filled in the receptacles 302 to a fill line 304 (shown in FIG. 13, in the desired openings 302). Although not shown in FIG. 14, the openings in FIGS. 13 and 14 are also labeled with column designations and row designations (in a matrix-type arrangement) so that each opening can be uniquely identified and so that a pik 150 can be placed in the corresponding positions of the holder 100 to register with receptacles 302 in which antigens are placed. The well tray 300 has an integral flange 306 for stability, and the upper corner 308 is chamfered or bevelled or rounded so as to facilitate placing a holder 100 thereover. As shown in FIG. 14, one corner 310 of the well tray is flattened so that a corresponding flattened portion of the holder 100 will register therewith to assure proper orientation of the holder relative to the well tray at all times. As shown in FIG. 14, the arrangement of FIGS. 13 and 14 has a total of 60 wells (6 columns and 10 rows). The holder used therewith will correspondingly hold 60 piks.

In the arrangement of FIGS. 13 and 14, the antigens may be pre-loaded at a factory, and a peel-off shipping seal 350 (FIG. 15) may be applied over the upper surface of the well tray 300 to prevent leakage and contamination of antigens during shipping. The flattened surface 310 of the well tray 300 enables a portion of the peel-off shipping seal 350 to extend thereover to provide a gripping tab for easy removal of the seal 350 when it is desired to use the device. The antigen could alternatively be loaded in the practitioner's office, and the seal 350 could thereafter be attached.

Figure 15:
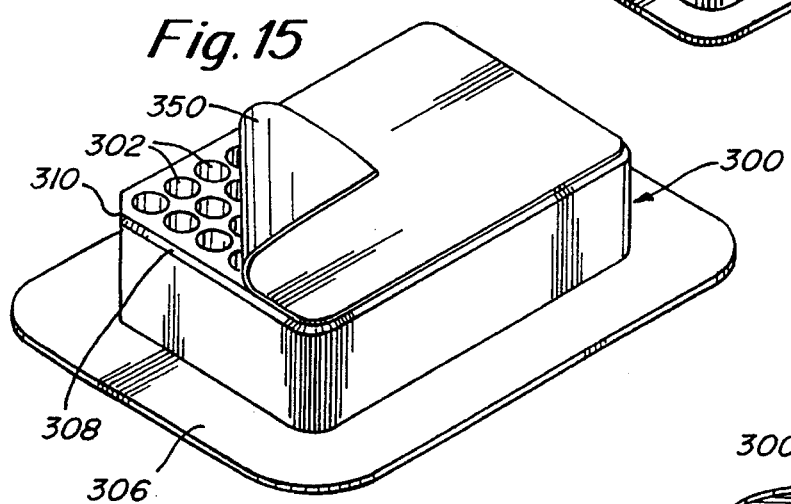
FIG. 15 shows the well tray of FIGS. 13 and 14, in perspective, with a peel-off seal member to prevent leakage and/or cross-contamination of antigens when shipped pre-loaded with antigens.
Figure 17:
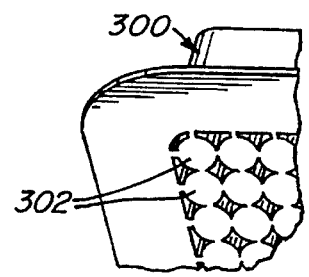
FIG. 17 illustrates a portion of the underside of the well tray of FIG. 15.

FIG. 17 shows the bottom surface of the well tray 300 of FIGS. 13-15 in greater detail showing a honeycomb-like underside of the tray which results from the molding of the receptacles 302.

Figure 16:
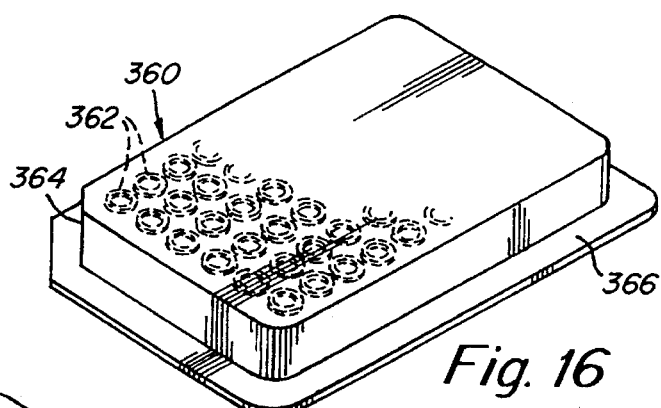
FIGS. 16 and 16A shows an airtight storage cover for use with the well tray of FIGS. 13 and 14, in place of the peel-off seal member of FIG. 15.
Figure 16A:
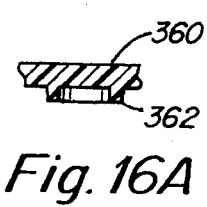

FIG. 16 shows a storage cover 360 which can be used in place of the shipping seal 350 over the well tray 300 which is pre-loaded with antigens at a factory, or which is pre-loaded with antigens by a practitioner shortly before use. The cover 360 has individual well sealing rings 362 projecting downwardly therefrom (see FIG. 16A), the rings 362 engaging tightly inside the upper opening of the receptacles 302 to seal the receptacles and to prevent leakage and cross-contamination. The cover 360 has a flattened surface 364 which engages with the flattened surface 310 of the well tray to provide proper orientation at all times. Also, a flange 366 is provided around the airtight storage cover 360 to enable easy insertion and removal of the airtight storage cover 360. After the airtight storage cover 360 is placed on the well tray 300 with the sealing rings 362 engaged with respective openings 302, it may be difficult to remove the airtight storage cover. However, the practitioner can place the well tray on a flat surface and hold it down by gripping the flange 306. Then, with the other hand, the flange 366 of the cover 360 can be gripped to facilitate pulling same upwardly to remove same from the well tray 300.

The well trays and holders of the present invention can be preferably molded from plastic materials by injection molding, to provide inexpensive and easy-to-make members. In preferred embodiment, the devices can be either disposable after one use, or can be made of plastic materials which can be sterilized for re-use, as desired. Sterilizable injection moldable plastic materials are well known in the art, and can be, for example, acetal, Celcon, Delrin, nylon, or other suitable plastics. The peel-off shipping seal 350 can be removably adhered to the upper surface of the well tray 300 by adhesives generally known in the art, and which do not disadvantageously interact with any antigens which may be stored in the receptacles 302.

The piks used in the above described embodiments of the present invention are modified forms of piks which are well known in the art, for example the DermaPik manufactured by Greer Laboratories, Inc., and which are shown in U.S. Pat. No. 4,237,906, the entire contents of which are incorporated herein by reference. The known Greer DermaPik is used substantially as presently exists, but with the upper handling member thereof shortened so that the cover member 110 of the holder 100 of the present invention can be thinner, thereby reducing the overall height of the device. The handling upper portion of the Greer DermaPik can be shortened since it is no longer necessary to manually handle the pik in the present invention, as is required when using the Greer system. If the upper portions 152 of the respective piks are not shortened (i.e. if the piks of U.S. Pat. No. 4,237,906 are not modified), they still may be used, but the overall height of the device will be greater. The elongated tapered shaft portion (lower portion) of the respective piks 150 could be shortened or made with a smaller diameter, as desired. If the piks are made with the smaller diameters for both the upper and lower portions thereof, a higher density of piks can be achieved.

The allergen containers shown in FIG. 11 are slightly modified forms of the existing allergen containers sold by Greer Laboratories, Inc. for use in the Dermapik system. However, any type of allergen well or container could be used, as desired, depending upon the corresponding design of the well tray of the present invention as described hereinabove.

Figure 18:
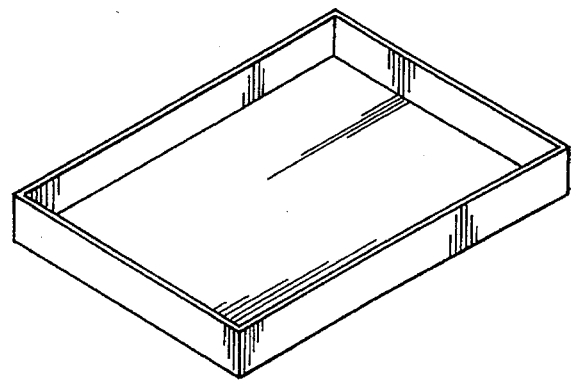
FIG. 18 shows a lower tray or cover for covering the bottom of a holder of FIG. 1.

As shown in FIG. 18, in reduced size, a box-like tray can be provided into which a holder 100 can be inserted after it is loaded with piks 150 by a practitioner in order to protect the piks from contamination. By using such a box member of FIG. 18 to store pre-loaded holders, the practitioner can prepare several holders in advance for quick use one-after-the-other. Alternatively, a peel-off sealing layer 190 can be provided, as shown in FIG. 8 in dashed lines, to protect any pre-loaded piks 150 and to keep contamination out. In the case where a foam strip 130 is used instead of the bellows 180, the peel-off sealing layer 190 is applied to the lower surface of the foam strip to achieve a similar effect. The peel-off sealing layer can be applied by the practitioner, or can be pre-applied in a factory before shipping. When the system is to be used, the peel-off sealing layer 190 can be easily removed by the practitioner (for example by pulling off at a projecting tab portion 192) and peeling same off of the device. The peel-off sealing layer 190 of FIG. 8 and the peel-off sealing layer 350 of FIG. 15 can be made of plastic materials or metal foil, as desired, and/or may be multi-layered to prevent reaction with the allergens or the like and to provide improved strength, as desired.

Also, as should be clear, different models may be manufactured with different spacing of needles, different numbers of needles, different types of needles, etc., as desired. The main feature of the present invention is the complete flexibility of the system whereby arrangement, orientation and spacing of the needles can be completely and fully selectable by the practitioner, as desired.

Figure 19:
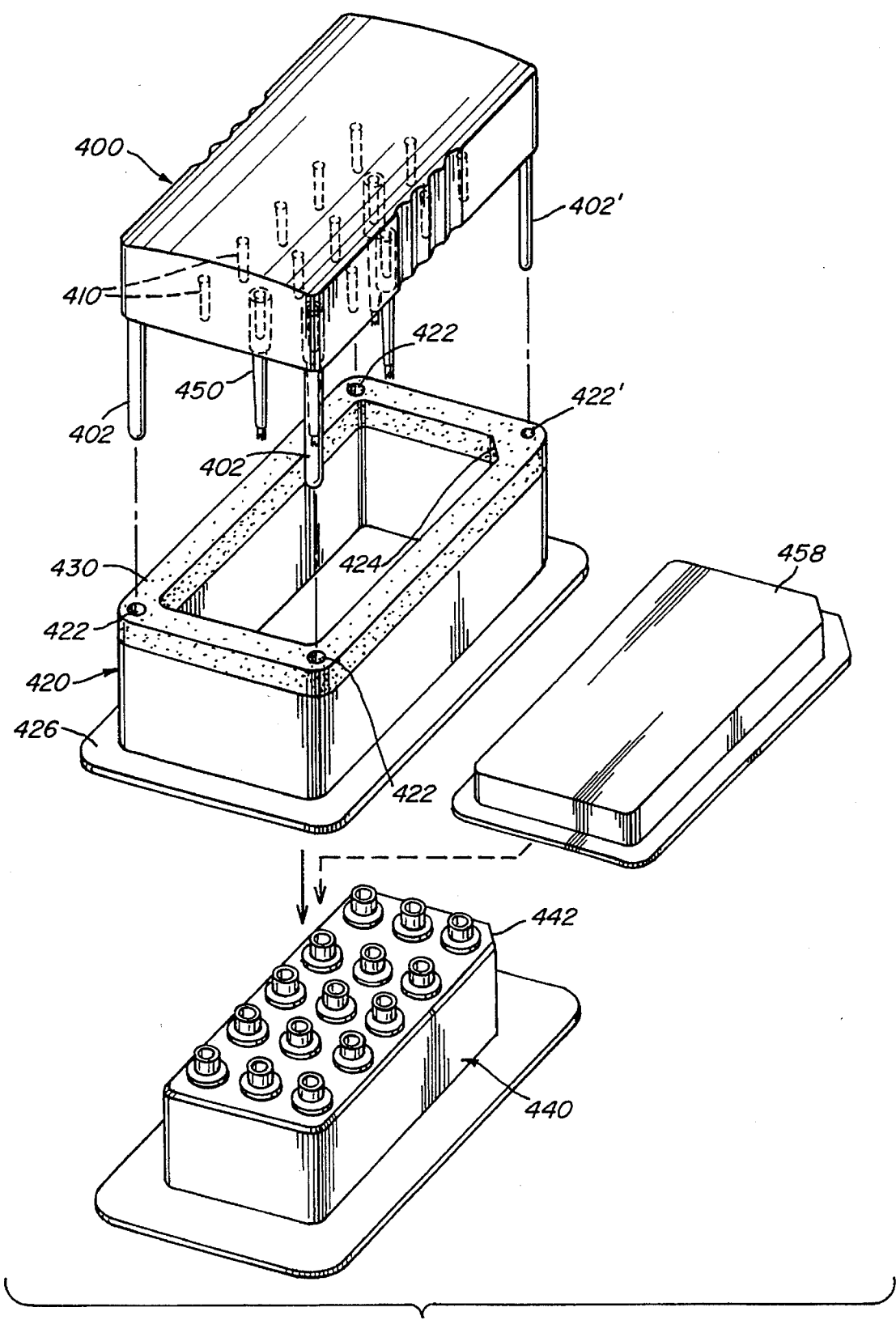
FIG. 19 shows a modified embodiment of a holder and well tray arrangement of the present invention.

FIG. 19 illustrates another embodiment of the invention wherein the holder is replaced with a two-piece holding apparatus which includes an upper pik holding member 400 and a lower collar member 420 which are interengageable with each other. The lower well tray 440 is similar to the previously described well trays, except that it holds existing antigen containers presently manufactured by Greer Laboratories, Inc. for use in the DermaPik system manufactured by Greer Laboratories, Inc. An upper tray 458 is provided for covering the upper portion of the well tray, the cover 458 being similar to the cover 220 shown in FIG. 1.

The upper holder member 400 includes alignment posts 402 extending downwardly therefrom which are receivable in alignment or registration holes 422 in the collar 420. In order to ensure proper orientation of the upper member 400 with the collar 420, one of the alignment posts 402' can be made smaller in diameter and its associated registration hole 422' can be made likewise smaller in diameter so that the upper member 400 is mountable on the collar 420 in only one orientation. The upper member 400 has posts 410 extending downwardly therefrom (described in detail with respect to FIGS. 20 and 21) on which are mounted piks 450. The piks 450 are identical to the existing Greer Laboratories crown needles for use in the DermaPik system manufactured by Greer Laboratories, Inc.

The upper surface of the collar has a foam strip 430 thereon against which the upper member 400 bears during use. The foam strip 430 serves the purpose of the foam strip 130 of the embodiment of FIG. 1 and acts a spring member. The collar member has a flange 426 extending therearound for location of the device on the skin of a patient and to provide a more comfortable engagement with the skin of the patient.

The well tray has a flat portion 442 thereon which is provided for registration with flat portion 424 of the collar so that the collar 420 is insertable in only one direction relative to the well tray 440.

Figure 20:
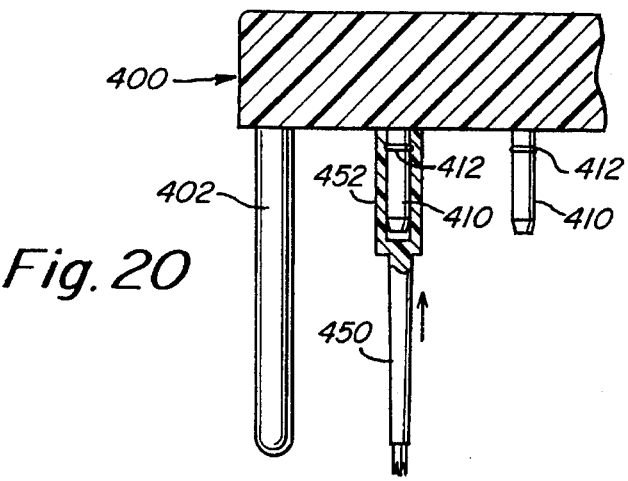
FIG. 20 is a partial sectional view showing details of the embodiment of FIG. 19.

FIG. 20 is an enlarged sectional view showing the upper portion 400 having the alignment posts 402 extending downwardly therefrom. FIG. 20 also shows the posts 410 on which the piks 450 are mountable. The posts 410 may have an annular projection 412 thereon and the inner surface of the piks 450 can have an annular depression therein in order to provide a snap fit of the pik 450 over the post 410. The post 410 is preferably tapered so as to force fit into a recess in the upper portion 452 of the pik 450 in order to provide secure engagement. The snap fit provided by the annular projection 412 further improves retention of the pik 450 on the post 410. After use, the piks 450 can be manually pulled off of the posts and disposed of.

Figure 21:
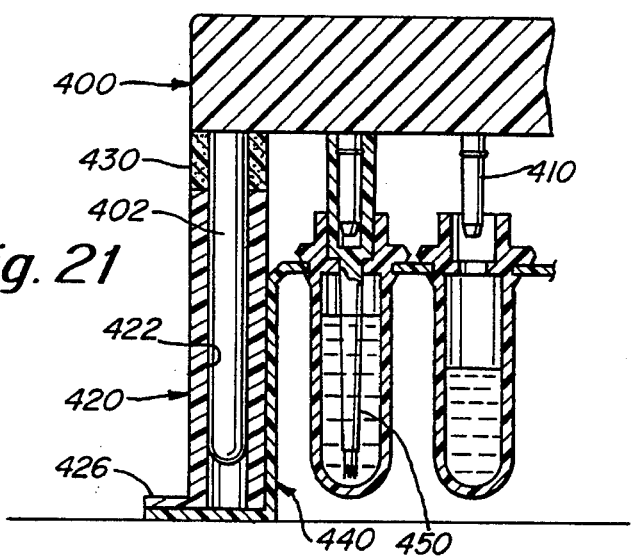
FIG. 21 is a partial sectional view showing the embodiment of FIG. 20 placed over a well tray.
Figure 22:
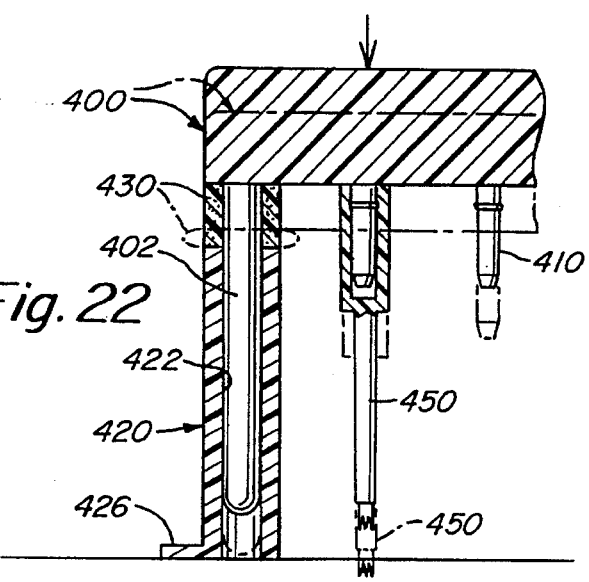
FIG. 22 shows the embodiment of FIGS. 20 and 21, in use to apply allergen to a skin of a patient.

FIG. 21 shows the arrangement of FIG. 20 mounted on a collar 420 which in turn is mounted on a well tray 440 so as to apply antigen to the pik 450. The antigen containers may be identical to the existing Greer Laboratory antigen containers, or can be as shown in FIG. 11, or can take any other desired form. Still further, the well tray 440 can be replaced by an integrally molded well tray such as that shown in FIG. 13, which has integrally formed antigen containers. After the system is interconnected as shown in FIG. 21, the collar 420 with the upper member 400 engaged thereon is removed and is applied to the skin, as shown in FIG. 22. Upon depressing of the upper member 400 to the dashed line position shown in FIG. 22, the pik penetrates the skin of the patient by a depth controlled by the compression of the foam 430.

Figure 23:
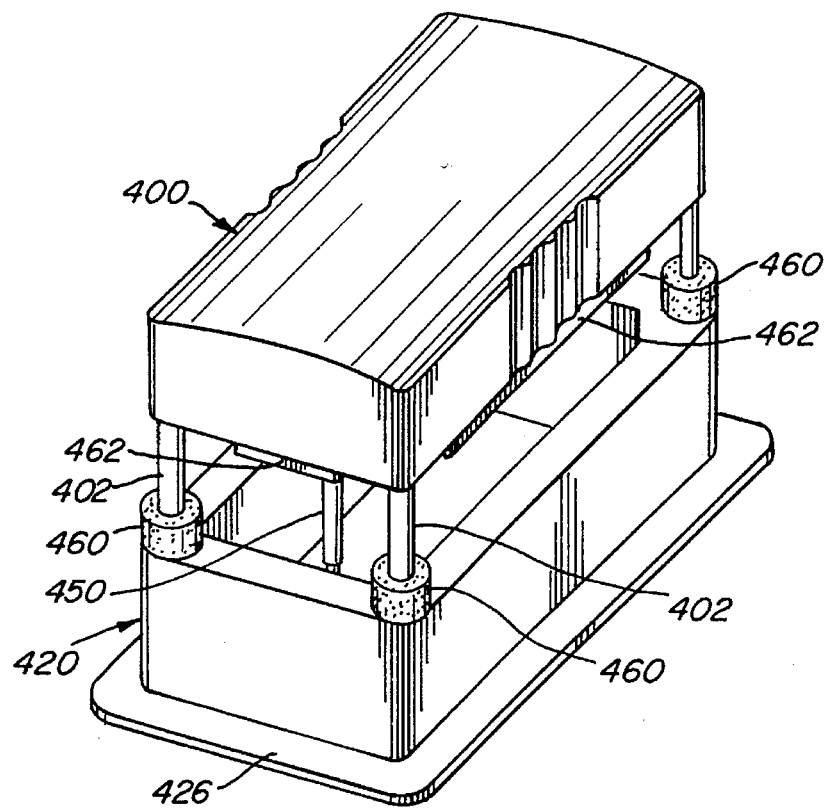
FIGS. 23 and 24 show a modified embodiment of the arrangement of FIG. 19, prior to use (FIG. 23) and during use (FIG. 24).
Figure 24:
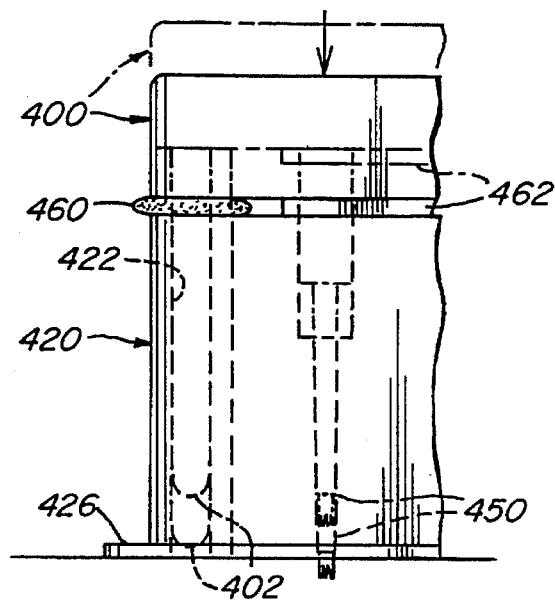

FIG. 23 shows a further modified embodiment wherein rings of foam 460 are used in place of the foam strip 430, but serve the same purpose. The system further comprises ribs 462 which serve as a "stop" to prevent excessive downward movement of the upper member 400 relative to the collar 420. The ribs 462 contact the upper surface of the collar when the maximum downward movement is achieved, thereby positively controlling depth of penetration of the piks 450.

As should be readily apparent, various modifications and alterations can be made to the above-described embodiments within the scope of the invention as defined by the accompanying claims. In particular, various features and characteristics of the various embodiments can be interchanged, as desired, consistent with their respective functions, within the scope of the appended claims.

What is claimed is:

1. An allergy testing apparatus for testing a patient for a plurality of substances, comprising:

a first member having a plurality of engaging means arranged at respective positions on said first member for selectively engaging a respective pricking or piercing element;

a plurality of pricking or piercing elements which are selectively engaged with selected engaging means of said first member, at selected positions on said first member, said pricking or piercing elements extending in a given direction from said first member for pricking or piercing the skin of a patient in use;

said first member having a side wall extending in said given direction so as to at least partly surround said pricking or piercing elements, said side wall having a free end portion for placement against the skin of a patient;

said side wall of said first member including a resilient compressible portion for controlling a downward movement distance of said pricking or piercing elements which are engaged with said first member;

a well tray having a plurality of receptacles for receiving substances for which a patient is to be tested at selected receptacles corresponding in position to the pricking or piercing elements which are engaged with said selected engaging means at said selected positions of said first member, said first member with said pricking or piercing elements engaged thereon, being engageable with said well tray for causing the pricking or piercing elements mounted to said first member to contact said substances in respective associated receptacles, said first member being thereafter removable from said well tray for application of said substances to a patient;

said removed first member then being adapted to be placed with said free ends of said side walls thereof against the skin of a patient and to be pressed downwardly against the skin of the patient to compress said compressible portion and to cause said pricking or piercing elements to contact the skin of the patient and to apply said substances at respective spaced apart positions on the skin of the patient, the respective spaced apart positions on the skin of the patient being spaced apart a distance corresponding to the positions at which the pricking or piercing elements are engaged with said first member.

2. The allergy testing apparatus of claim 1, wherein:

said first member comprises a block-like member with said side wall extending from said block-like member; and said plurality of engaging means of said first member comprises a plurality of openings in said block-like member, said plurality of pricking or piercing elements comprising elongated elements which are selectively insertable in selective openings of said block-like member.

3. The allergy testing apparatus of claim 2, further comprising locking means for lockingly engaging said elongated elements in said openings of said block-like member to prevent tipping or tilting of said elongated elements in said block-like member.

4. The allergy testing apparatus of claim 3, wherein said locking means comprises a cover member which is engageable with said block-like member to contact and engage upper portions of said elongated elements when said cover member is engaged with said block-like member.

5. The allergy testing apparatus of claim 4, wherein said cover member is hingedly connected to said block-like member.

6. The allergy testing apparatus of claim 1, wherein said resilient compressible portion comprises a foam portion at said free end portion of said side wall of said first member, for contacting the skin of a patient.

7. The allergy testing apparatus of claim 1, wherein said resilient compressible portion comprises a bellows portion on said side wall of said first member.

8. The allergy testing apparatus of claim 1, wherein said first member comprises indicia for uniquely marking each of said plurality of engaging means, and wherein said well tray has indicia thereon for uniquely marking each receptacle, so that a substance can be inserted into selected uniquely marked receptacles corresponding to the uniquely marked engaging means in which a pricking or piercing elements is engaged.

9. The allergy testing apparatus of claim 4, wherein said engaging means comprises a plurality of openings in said first member, and a plurality of openings in said cover member which are in registration with said openings of said first member, said pricking or piercing elements each having a portion which is engageable in said openings of said first member and of said cover member to prevent tilting of said pricking or piercing elements relative to said first member during use.

10. The allergy testing apparatus of claim 1, wherein said receptacles of said well tray are arranged for receiving respective containers containing substances for which a patient is to be tested.

11. The allergy testing apparatus of claim 1, wherein said well tray comprises a seal thereon for sealing said plurality of receptacles.

12. The allergy testing apparatus of claim 11, wherein seal is applied after placing substances in a plurality of respective receptacles.

13. The allergy testing apparatus of claim 1, further comprising a cover for removably covering said well tray to cover said receptacles thereof.

14. The allergy testing apparatus of claim 13, wherein said well tray and said cover each include a registration element for permitting orientation of said cover on said well tray in only one direction.

15. The allergy testing apparatus of claim 1, wherein said first member and said well tray each include a registration element for permitting engagement of said first member with said well tray in only one direction.

16. The allergy testing apparatus of claim 1, wherein said engaging means of said first member comprises a plurality of elongated members extending from said first member for engaging respective pricking or piercing elements.

17. The allergy testing apparatus of claim 16, wherein said elongated members have snap-type engaging means for snappingly engaging said pricking or piercing elements mounted thereon.

18. The allergy testing apparatus of claim 1, wherein said first member comprises:

a lower hollow member which includes said side wall; and an upper member which is slidably engageable with said lower member, said upper member including said plurality of engaging means thereon, and said upper and lower members being movable relative to each other during use; and a guide for guiding movement of said upper member relative to said lower member during use.

19. The allergy testing apparatus of claim 18, wherein said resilient compressible portion is arranged between said upper and lower members.

20. The allergy testing apparatus of claim 18, wherein said upper member is engageable with said well tray for applying substances to pricking or piercing elements for application to the skin of a patient.

21. The allergy testing apparatus of claim 1, wherein said resilient compressible portion controls a depth of penetration of said pricking or piercing elements in the skin of a patient by permitting a limited amount of compression of said resilient compressible portion.

22. The allergy testing apparatus of claim 1, wherein said resilient compressible member comprises a foam member coupled to a lower portion of said first member for contacting the skin of a patient.

23. The allergy testing apparatus of claim 1, wherein said resilient compressible member comprises a bellows portion on said first member.

24. The allergy testing apparatus of claim 1, wherein said first member comprises indicia for uniquely marking each of said plurality of openings, and wherein said well tray has indicia thereon for uniquely marking each receptacle, so that a substance can be inserted into selected uniquely marked receptacles corresponding to the uniquely marked openings in which a pricking or piercing element is engaged.

25. An allergy testing apparatus for testing a patient for a plurality of substances, comprising:

a first member having a plurality of engaging means arranged at respective positions on said first member for selectively engaging a respective pricking or piercing element;

a plurality of pricking or piercing elements which are selectively engaged with selected engaging means of said first member, at selected positions on said first member, said selected engaging means and said plurality of pricking or piercing elements both being fewer in number than said plurality of engaging means of said first member, and said pricking or piercing elements extending in a given direction from said first member for pricking or piercing the skin of a patient in use; and a well tray having a plurality of receptacles for receiving substances for which a patient is to be tested at selected receptacles corresponding in position to the pricking or piercing elements which are engaged with said selected engaging means at said selected positions of said first member, said first member with said pricking or piercing elements engaged thereon, being engageable with said well tray for causing the pricking or piercing elements mounted to said first member to contact said substances in respective associated receptacles, said first member being thereafter removable from said well tray for application of said substances to a patient;

said removed first member then being adapted to be placed against the skin of a patient and to be pressed downwardly against the skin of the patient to cause said pricking or piercing elements to contact the skin of the patient and to apply said substances at respective spaced apart positions on the skin of the patient, the respective spaced apart positions on the skin of the patient being spaced apart a distance corresponding to the positions at which the pricking or piercing elements are engaged with said first member.

26. The allergy testing apparatus of claim 25, wherein:

said first member comprises a block-like member; and said engaging means of said first member comprises a plurality of openings in said block-like member, said plurality of pricking or piercing elements comprising elongated elements which are selectively insertable in selective openings of said block-like member.

27. The allergy testing apparatus of claim 26, further comprising locking means for lockingly engaging said elongated elements in said openings of said block-like member to prevent tipping or tilting of said elongated elements in said block-like member.

28. The allergy testing apparatus of claim 27, wherein said locking means comprises a cover member which is engageable with said block-like member to contact and engage upper portions of said elongated elements when said cover member is engaged with said block-like member.

29. The allergy testing apparatus of claim 28, wherein said cover member is hingedly connected to said block-like member.

30. The allergy testing apparatus of claim 25, wherein said first member comprises indicia for uniquely marking each of said plurality of engaging means, and wherein said well tray has indicia thereon for uniquely marking each receptacle, so that a substance can be inserted into selected uniquely marked receptacles corresponding to the uniquely marked engaging means in which a pricking or piercing elements is engaged.

31. A method of testing a patient for a plurality of allergies at substantially the same time, comprising:

providing a first member having a plurality of engaging means arranged at respective positions on said first member;

providing a plurality of pricking or piercing elements which are selectively engageable with the selected engaging means of said first member, at selected positions on said first member, for pricking or piercing the skin of a patient in use;

providing a well tray having a plurality of receptacles for respectively receiving substances for which a patient is to be tested;

loading respective receptacles of said well tray with substances for which a patient is to be tested;

engaging a plurality of pricking or piercing means in engaging means of said first member which are in registration with the receptacles of said well tray in which substances have been loaded;

engaging said well tray with said first member to cause said plurality of pricking or piercing elements to contact the substances in the loaded receptacles of said well tray;

removing said first member from engagement with said well tray means; and placing a wall of said first member, after removal of said first member from said well tray, against the skin of a patient with said wall maintaining said pricking or piercing elements out of contact with the skin of the patient and compressing a resiliently compressible portion of said first member to cause said pricking or piercing elements to move toward the skin of the user to contact and prick the skin of the user for applying substances which have contacted said pricking or piercing elements to said skin of said patient.

32. The method of claim 31, wherein said step of applying comprises rocking said first member, relative to the skin of the patient, while applying a force toward the skin of the user, to contact the skin of the patient with said pricking or piercing elements.

33. The method of claim 31, wherein said first member has indicia thereon for uniquely identifying respective engaging means, and said well tray has indicia thereon for correspondingly uniquely identifying said receptacles so that substances can be placed in receptacles corresponding in position to the engaging means to which a pricking or piercing element is engaged.

34. The method of claim 31, comprising engaging said pricking or piercing elements with less than the total number of engaging means of said first member.

35. An allergy testing apparatus for testing a patient for a plurality of substances, comprising:

a first member having a plurality of opening therein, said openings being arranged at respective positions on said first member, said openings selectively receiving a respective pricking or piercing element therein;

a plurality of pricking or piercing elements which are selectively received in openings of said first member, at selected positions on said first member, for pricking or piercing the skin of a patient at spaced apart positions in use;

a resilient compressible member coupled to said first member for controlling a downward movement distance of said first member and for consequently controlling a downward movement distance of said pricking or piercing elements which are engaged with said first member;

a locking device arranged to lockingly engage said pricking or piercing elements in respective openings of said first member to prevent tipping or tilting of said pricking or piercing elements in said first member, said locking device comprising a cover member which is engageable with said first member to contact and engage upper portions of said pricking or piercing elements when said cover member is engaged with said first member; and a well tray having a plurality of receptacles for receiving substances for which a patient is to be tested at selected receptacles corresponding in position to the pricking or piercing elements which are received in openings said selected engaging means at selected positions of said first member, said first member with said pricking or piercing elements, being engageable with said well tray for causing the pricking or piercing elements to contact said substances in respective associated receptacles, said first member being thereafter removable from said well tray for application of said substances to a patient;

said removed first member then being adapted to be placed against the skin of a patient and to be pressed downwardly against the skin of the patient to compress said compressible means and to cause said pricking or piercing elements to contact the skin of the patient and to apply said substances at respective spaced apart positions on the skin of the patient.

36. The allergy testing apparatus of claim 35, wherein:

said first member is a block-like member having said plurality of openings therein; and said plurality of pricking or piercing elements comprises elongated elements which are selectively insertable in said openings of said block-like member.

37. The allergy testing apparatus of claim 36, wherein said cover member is hingedly connected to said block-like member.

38. The allergy testing apparatus of claim 35, wherein said cover member is hingedly connected to said block-like member.

39. The allergy testing apparatus of claim 35, wherein said cover member has a plurality of openings therein which are in registration with said openings of said first member, said pricking or piercing elements each having a portion which is engageable in said openings of said first member and of said cover member to prevent tilting of said pricking or piercing elements relative to said first member during use.

* * * * *